US011717178B2

(12) United States Patent
Oode et al.

(10) Patent No.: US 11,717,178 B2
(45) Date of Patent: Aug. 8, 2023

(54) MEASUREMENT SENSOR PACKAGE AND MEASUREMENT SENSOR

(71) Applicant: KYOCERA Corporation, Kyoto (JP)

(72) Inventors: Yasushi Oode, Kirishima (JP); Hiroki Ito, Kirishima (JP); Yoshimasa Sugimoto, Kirishima (JP); Noritaka Niino, Kirishima (JP); Shogo Matsunaga, Kirishima (JP); Takuya Hayashi, Kirishima (JP)

(73) Assignee: KYOCERA Corporation, Kyoto (JP)

( * ) Notice: Subject to any disclaimer, the term of this patent is extended or adjusted under 35 U.S.C. 154(b) by 766 days.

(21) Appl. No.: 15/778,651

(22) PCT Filed: Nov. 10, 2016

(86) PCT No.: PCT/JP2016/083434
§ 371 (c)(1),
(2) Date: May 24, 2018

(87) PCT Pub. No.: WO2017/130520
PCT Pub. Date: Aug. 3, 2017

(65) Prior Publication Data
US 2018/0353087 A1   Dec. 13, 2018

(30) Foreign Application Priority Data

Jan. 25, 2016   (JP) ................................. 2016-011937

(51) Int. Cl.
*A61B 5/0285* (2006.01)
*G01P 5/26* (2006.01)
(Continued)

(52) U.S. Cl.
CPC .......... *A61B 5/0285* (2013.01); *A61B 5/0059* (2013.01); *A61B 5/0261* (2013.01);
(Continued)

(58) Field of Classification Search
CPC . A61B 5/0285; A61B 5/0059; A61B 5/02141; A61B 5/0261; A61B 5/7203;
(Continued)

(56) References Cited

U.S. PATENT DOCUMENTS 5,684,308 A * 11/1997 Lovejoy .............. H01L 27/1443
257/E27.128
6,166,403 A * 12/2000 Castagnetti ........... H01L 23/552
257/208

(Continued)

FOREIGN PATENT DOCUMENTS

CN     101371373 A     2/2009
EP      1993148 A1    11/2008
(Continued)

*Primary Examiner* — Jonathan Cwern
*Assistant Examiner* — Amy Shafqat
(74) *Attorney, Agent, or Firm* — Volpe Koenig

(57) ABSTRACT

A measurement sensor package and a measurement sensor reduce susceptibility to noise and enable highly accurate measurement. A measurement sensor package includes a substrate. The substrate includes a first recess including a first bottom surface on which a light emitter is mountable, and a first step surface having a first connection pad thereon, a second recess including a second bottom surface on which a light receiver is mountable, and a second step surface having a second connection pad thereon. In a direction connecting a center of the first bottom surface and a center of the second bottom surface in a plan view, the first step surface is located outward from the first bottom surface and the second step surface is located outward from the second bottom surface.

14 Claims, 8 Drawing Sheets

(51) Int. Cl.
*A61B 5/00* (2006.01)
*A61B 5/021* (2006.01)
*A61B 5/026* (2006.01)

(52) U.S. Cl.
CPC ........ *A61B 5/02141* (2013.01); *A61B 5/7203* (2013.01); *G01P 5/26* (2013.01); *A61B 2562/0233* (2013.01); *A61B 2562/182* (2013.01)

(58) Field of Classification Search
CPC ...... A61B 2562/182; A61B 2562/0233; A61B 5/026; A61B 5/6826; G01P 5/26; H01L 23/60
See application file for complete search history.

(56) References Cited

U.S. PATENT DOCUMENTS

| | | | | |
|---|---|---|---|---|
| 6,300,659 B1* | 10/2001 | Zhang | ................ | H01L 21/2022 257/347 |
| 6,392,256 B1* | 5/2002 | Scott | .................... | H01L 31/105 372/50.1 |
| 6,519,379 B1* | 2/2003 | Izawa | ................ | G02B 6/12002 369/44.12 |
| 6,574,254 B1* | 6/2003 | Wang | ................ | H01S 5/02248 372/34 |
| 6,639,887 B1* | 10/2003 | Izawa | .................... | G11B 7/124 369/112.07 |
| 6,683,512 B2* | 1/2004 | Nakamata | ................ | H01L 23/66 333/126 |
| 6,897,551 B2* | 5/2005 | Amiotti | ................ | B81C 1/00285 257/682 |
| 7,156,562 B2* | 1/2007 | Mazotti | ................ | G02B 6/4246 385/88 |
| 7,667,324 B2* | 2/2010 | Wang | ................ | B81C 1/00269 257/738 |
| 8,076,785 B2* | 12/2011 | Nishimura | ......... | H01L 23/3128 257/780 |
| 8,232,883 B2* | 7/2012 | Yao | ....................... | G01J 1/0214 340/600 |
| 8,309,461 B2* | 11/2012 | Krestnikov | ............ | H01L 24/73 438/667 |
| 8,362,496 B1* | 1/2013 | Tu | ....................... | H01L 23/3107 257/82 |
| 8,575,650 B2* | 11/2013 | Ishibashi | ............. | H01L 31/1075 257/186 |
| 8,591,426 B2* | 11/2013 | Onoe | .................. | A61B 5/6838 600/504 |
| 8,755,644 B2* | 6/2014 | Budd | .................. | G02B 6/4206 385/14 |
| 9,133,024 B2* | 9/2015 | Phan | ................ | B01L 3/502746 |
| 9,322,901 B2* | 4/2016 | Kerness | ................ | G01S 7/4813 |
| 9,439,569 B2* | 9/2016 | Shimuta | ................ | A61B 5/14551 |
| 9,490,239 B2* | 11/2016 | Schubert | ............. | H05B 47/105 |
| 9,530,941 B2* | 12/2016 | Jeon | ...................... | H01L 33/382 |
| 9,811,713 B2* | 11/2017 | Pi | ........................... | G06F 21/32 |
| 10,024,655 B2* | 7/2018 | Raguin | ................ | A61B 5/117 |
| 10,121,918 B2* | 11/2018 | Chang | .................. | G01S 7/4813 |
| 10,175,107 B2* | 1/2019 | Shibayama | ........... | G01J 3/0286 |
| 10,265,020 B2* | 4/2019 | Yamashita | ......... | A61B 5/02416 |
| 10,290,993 B2* | 5/2019 | Chen | .................... | H01S 5/4025 |
| 10,672,697 B2* | 6/2020 | Funahashi | ............... | H01L 24/32 |
| 10,776,645 B2* | 9/2020 | Baek | .................... | G06K 9/2036 |
| 2004/0012099 A1* | 1/2004 | Nakayama | ........... | H01L 21/568 257/787 |
| 2004/0091006 A1* | 5/2004 | Nishiyama | ............ | H01S 5/0683 372/36 |
| 2004/0161002 A1* | 8/2004 | Kohara | ............... | H01S 5/02248 372/34 |
| 2006/0261360 A1* | 11/2006 | Takehashi | ............... | H01L 33/62 257/98 |
| 2007/0194427 A1* | 8/2007 | Choi | ........................ | H01L 24/73 257/686 |
| 2007/0223549 A1* | 9/2007 | Livshits | ............... | G02B 6/1228 372/45.01 |
| 2009/0202251 A1 | 8/2009 | Shibayama | | |
| 2010/0056887 A1* | 3/2010 | Kimura | ............... | A61B 5/14552 600/324 |
| 2012/0267674 A1* | 10/2012 | Watari | .................... | H01L 23/13 257/99 |
| 2013/0137994 A1* | 5/2013 | Sawada | .................. | G01N 21/49 600/479 |
| 2014/0346627 A1* | 11/2014 | Yamada | ............... | H04N 5/2253 257/431 |

FOREIGN PATENT DOCUMENTS

| | | |
|---|---|---|
| EP | 3395242 A1 | 10/2018 |
| JP | 2009099926 A * | 5/2009 |
| JP | 5031895 B | 9/2012 |

* cited by examiner

MEASUREMENT SENSOR PACKAGE AND MEASUREMENT SENSOR

FIELD

The present invention relates to a measurement sensor package and a measurement sensor.

BACKGROUND

Measurement sensors that easily and speedily measure biological information including blood flow have been awaited. Measurement of blood flow uses, for example, the Doppler effect of light. When blood is illuminated with light, the light is scattered by blood cells, such as red blood cells. The frequency of the illuminating light and the frequency of the scattered light are used to calculate the traveling speed of the blood cells.

One example of the measurement sensor for measuring blood flow is a self-luminous measurement sensor described in Patent Literature 1. The sensor includes a substrate, an illuminator arranged on the substrate to illuminate blood with light, a light receiver arranged on the substrate to receive scattered light, and a front plate bonded to the substrate with a light-shielding bond surrounding the illuminator and the light receiver.

The measurement sensor for measuring blood flow or other purposes can generate unintended electromagnetic waves that enter a signal wiring conductor and generate noise, which may then lower the measurement accuracy.

CITATION LIST

Patent Literature

Patent Literature 1: Japanese Patent No. 5031895

BRIEF SUMMARY

A measurement sensor package according to one aspect of the present invention includes a substrate including a plurality of dielectric layers stacked on one another. The substrate is a rectangular plate. The substrate includes a first recess for containing a light emitter and a second recess for containing a light receiver on a first surface of the substrate. The first recess includes a first bottom surface on which the light emitter is mountable, and an inner side surface having a first step with a first step surface extending in a plane direction of the first surface. The first step surface has a first connection pad thereon. The first connection pad is electrically connectable to the light emitter. The second recess includes a second bottom surface on which the light receiver is mountable, and an inner side surface having a second step with a second step surface extending in the plane direction of the first surface. The second step surface has a second connection pad thereon. The second connection pad is electrically connectable to the light receiver. In a direction connecting a center of the first bottom surface and a center of the second bottom surface in a plan view, the first step surface is located outward from the first bottom surface and the second step surface is located outward from the second bottom surface.

A measurement sensor according to another aspect of the present invention includes the measurement sensor package according to the above aspect, a light emitter contained in the first recess, and a light receiver contained in the second recess.

BRIEF DESCRIPTION OF DRAWINGS

The objects, features, and advantages of the present invention will become apparent from the following detailed description and the drawings.

DETAILED DESCRIPTION

Figure 1:
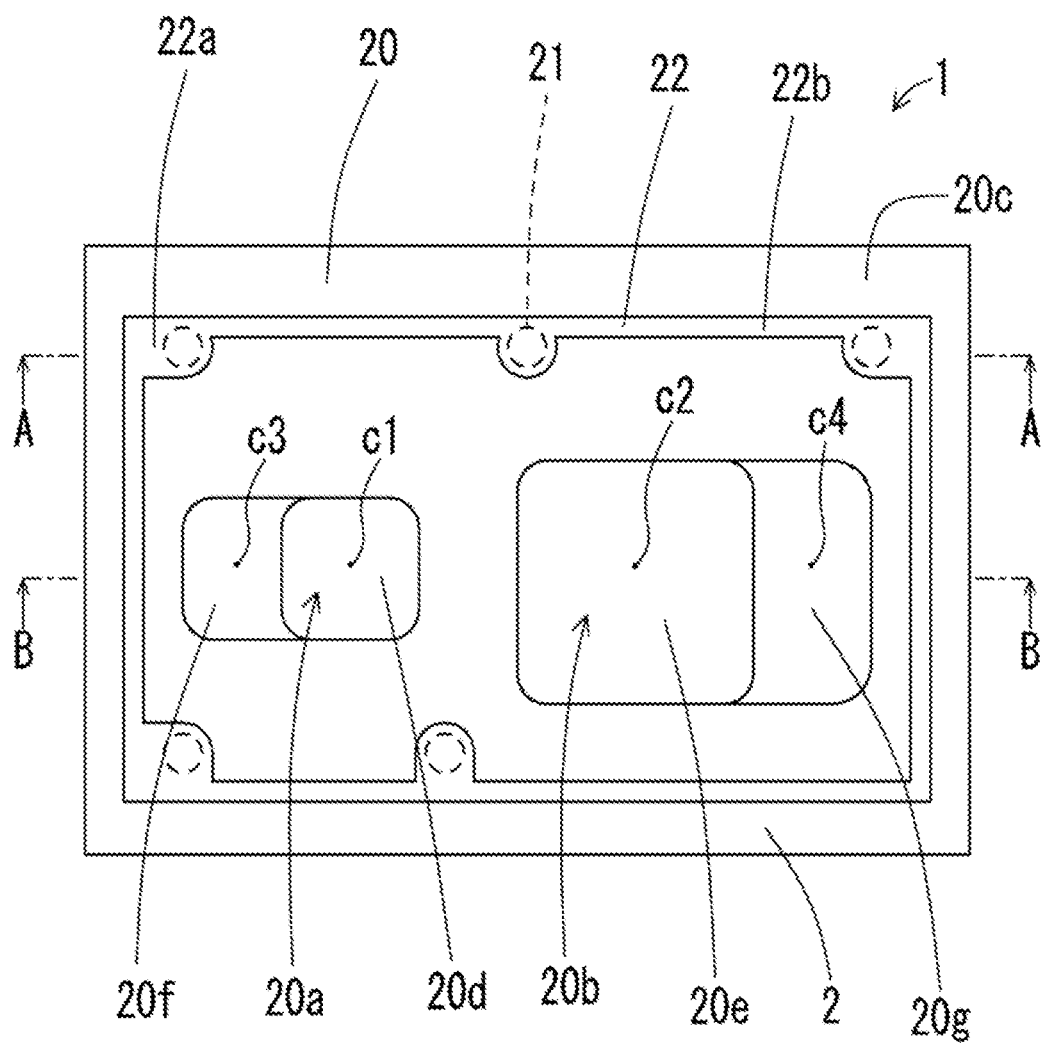
FIG. 1 is a plan view of a measurement sensor package 1 according to an embodiment of the present invention.
Figure 2:
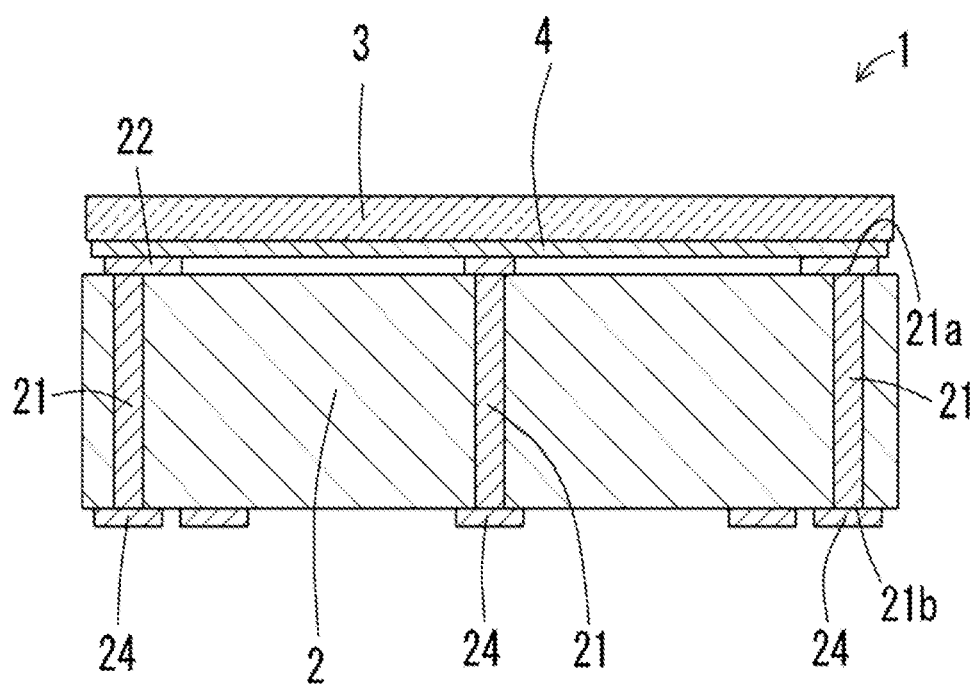
FIG. 2 is a cross-sectional view of the measurement sensor package 1 taken along line A-A of FIG. 1.
Figure 3:
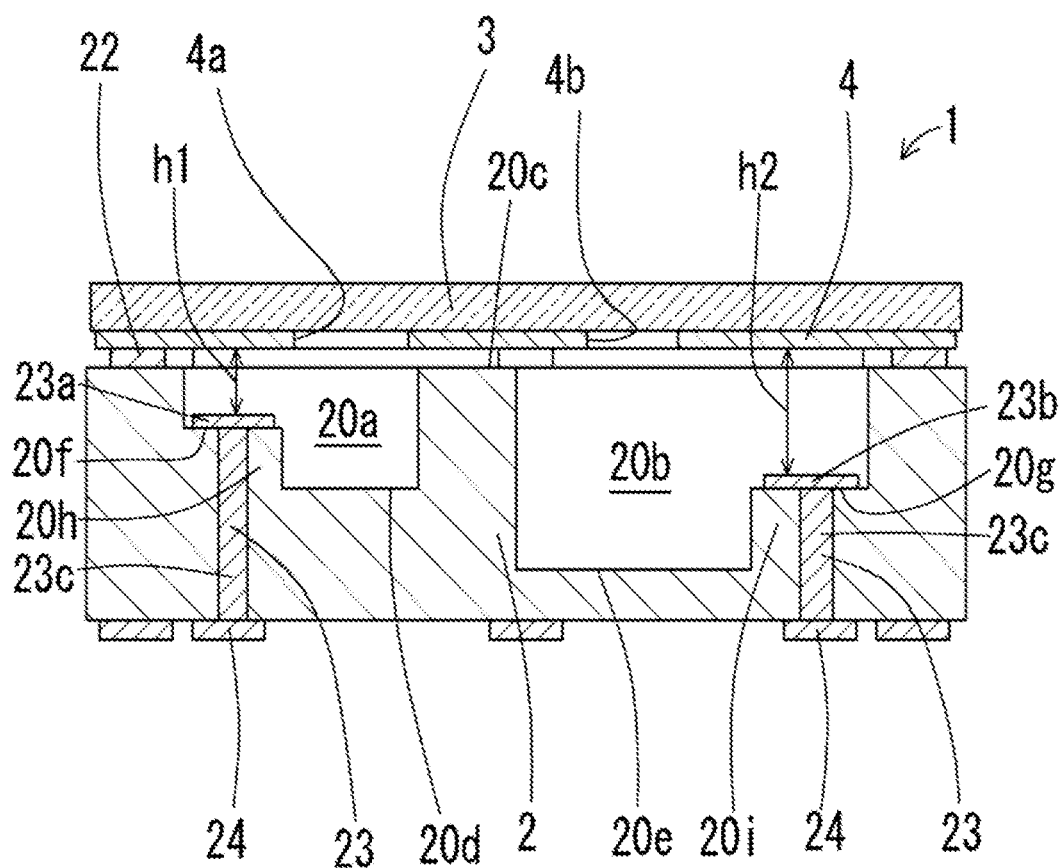
FIG. 3 is a cross-sectional view of the measurement sensor package 1 taken along line B-B of FIG. 1.

FIG. 1 is a plan view of a measurement sensor package 1 according to an embodiment of the present invention. FIG. 2 is a cross-sectional view of the measurement sensor package 1 taken along line A-A of FIG. 1. FIG. 3 is a cross-sectional view of the measurement sensor package 1 taken along line B-B of FIG. 1. In the plan view of FIG. 1, a lid 3, a ground conductor layer 4, and signal wiring conductors 23 are not shown.

The measurement sensor package 1 includes a substrate 2 containing a light emitter and a light receiver.

The substrate 2 according to the present embodiment is a rectangular plate, which includes multiple dielectric layers stacked on one another. The substrate 2 has at least two recesses, which are a first recess 20a to contain a light emitter, and a second recess 20b to contain a light receiver. The first recess 20a and the second recess 20b are open in a first surface (first main surface) 20c of the substrate 2.

The first recess 20a has a first bottom surface 20d, on which the light emitter is mountable. The first recess 20a has a first step 20h on its inner side surface. The first step 20h has a first step surface 20f, which extends in the plane direction of the first main surface 20c. A first connection pad 23a, which is electrically connected to the light emitter, is placed on the first step surface 20f. The second recess 20b has a second bottom surface 20e, on which the light receiver is mountable. The second recess 20b has a second step 20i on its inner side surface. The second step 20i has a second step surface 20g, which extends in the plane direction of the first main surface 20c. A second connection pad 23b, which is electrically connected to the light receiver, is placed on the second step surface 20g.

In the present embodiment, the first step surface 20f is located outward from the first bottom surface 20d, and the second step surface 20g is located outward from the second bottom surface 20e in a direction connecting a center c1 of the first bottom surface 20d and a center c2 of the second bottom surface 20e in a plan view. In the present embodiment, as in the plan view of FIG. 1, the direction connecting the center c1 of the first bottom surface 20d and a center c3 of the first step surface 20f is the same as the direction connecting the center c1 of the first bottom surface 20*d* and the center c2 of the second bottom surface 20*e*. The direction connecting the center c1 of the first bottom surface 20*d* and the center c3 of the first step surface 20*f* may differ from the direction connecting the center c1 of the first bottom surface 20*d* and the center c2 of the second bottom surface 20*e*. In the present embodiment, as in the plan view of FIG. 1, the direction connecting the center c2 of the second bottom surface 20*e* and a center c4 of the second step surface 20*g* is the same as the direction connecting the center c1 of the first bottom surface 20*d* and the center c2 of the second bottom surface 20*e*. The direction connecting the center c2 of the second bottom surface 20*e* and the center c4 of the second step surface 20*g* may differ from the direction connecting the center c1 of the first bottom surface 20*d* and the center c2 of the second bottom surface 20*e*.

In this structure, the first step surface 20*f* on which the first connection pad 23*a* is placed and the second step surface 20*g* on which the second connection pad 23*b* is placed prevent unintended electromagnetic waves generated in a measurement sensor from entering the first connection pad 23*a* and the second connection pad 23*b* and generating noise. In particular, a measurement sensor used for measuring blood flow or other purposes includes a light receiver that receives a relatively small amount of light and outputs a weak light receiving signal. An electromagnetic wave generated by a driving signal provided from the light emitter can interfere with the light receiving signal provided from the light receiver and cause electric cross-talk, which generates noise. In particular, a connection pad for electrically connecting a measurement sensor package to the light receiver usually has a large surface area, and thus easily receives electromagnetic waves generated by a driving signal provided from the light emitter. In the present embodiment, the first step surface 20*f* on which the first connection pad 23*a* is placed and the second step surface 20*g* on which the second connection pad 23*b* is placed are located outwardly in the direction connecting the centers c1 and c2 of the first and second bottom surfaces 20*d* and 20*e* in a plan view. A measurement sensor including the measurement sensor package 1 according to the present embodiment can thus reduce electric cross-talk resulting from electromagnetic waves generated by the driving signal provided from the light emitter interfering into a light receiving signal provided from the light receiver, and enables accurate measurement.

A self-luminous measurement sensor includes a light emitter that emits light to be scattered by a measurement object, and a light receiver that receives light scattered by the measurement object. When the optical path from the light emitter to the light receiver is shorter, the right receiver obtains more light. The measurement sensor including the measurement sensor package 1 according to the present embodiment includes the light emitter and the light receiver located inward. This shortens the optical path between the light emitter and the light receiver, and improves the sensitivity of the measurement sensor.

The measurement sensor including the measurement sensor package 1 according to the present embodiment includes a light-shielding wall that is thick enough to shield light between the light emitter and the light receiver in a plan view. The light emitter and the light receiver are arranged near the light-shielding wall. This structure reduces optical cross-talk caused by the light receiver directly receiving light emitted from the light emitter.

The first recess 20*a* and the second recess 20*b* according to the present embodiment may each have a circular, square, or rectangular opening, or an opening having another shape. The first recess 20*a* has an opening with, for example, a vertical dimension of 0.3 to 1.5 mm and a horizontal dimension of 0.3 to 2.0 mm. The second recess 20*b* has an opening with, for example, a vertical dimension of 0.5 to 2.0 mm and a horizontal dimension of 0.5 to 2.5 mm. The first recess 20*a* may have the same depth as or a different depth from the second recess 20*b* in the thickness direction of the substrate 2. In the embodiment shown in FIGS. 1 to 3, the first recess 20*a* has a smaller depth than the second recess 20*b*.

The measurement sensor package 1 according to the present embodiment also includes the lid 3 and the ground conductor layer 4.

The lid 3 is bonded to the first main surface 20*c* of the substrate 2 to cover the first recess 20*a* and the second recess 20*b*. The lid 3 is a plate formed from an insulating material. The lid 3 transmits light emitted from the light emitter contained in the first recess 20*a*, and light to be received by the light receiver contained in the second recess 20*b*.

The measurement sensor including the measurement sensor package 1 according to the present embodiment illuminates a finger, which is a measurement object, placed on the surface of the lid 3 with light emitted from the light emitter. The lid 3 formed from an electrically conductive material can allow, when the finger is placed on the lid 3, unintended electric charge accumulating in the fingertip to be discharged into the substrate 2 through the lid 3, and then generate noise. The lid 3 is formed from an insulating material, and thus does not allow unintended electric charge to flow through the lid 3.

The lid 3 transmits light applied to or scattered by a measurement object. The characteristics of the applied light and the scattered light depend on the light emitter used. The lid 3 may thus at least transmit the light emitted from the light emitter used. The lid 3 may be formed from an insulating material having a light transmittance of at least 70%, or specifically at least 90% for the wavelength of light emitted from the light emitter.

Examples of the insulating material for the lid 3 include a transparent ceramic material such as sapphire, a glass material, and a resin material. Examples of the glass material include borosilicate glass, crystallized glass, quartz, and soda glass. Examples of the resin material include a polycarbonate resin, an unsaturated polyester resin, and an epoxy resin.

The lid 3 is directly touched by a measurement object such as a finger, and thus needs a predetermined strength. The strength of the lid 3 is determined by the strength of its material and its thickness. The transparent ceramic material or glass material listed above can have sufficiently high strength when having at least a predetermined thickness. The lid 3 formed from a glass material may have a thickness of, for example, 0.05 to 5 mm.

The ground conductor layer 4 is arranged on a second main surface of the lid 3 facing the first recess 20*a* and the second recess 20*b*, which is a main surface opposite to a first main surface to be touched by the finger. The ground conductor layer 4 is connected to a ground potential. The ground conductor layer 4 has a first opening 4*a*, which allows passage of light emitted from the light emitter, and a second opening 4*b*, which allows passage of light to be received by the light receiver.

The ground conductor layer 4 functions as a mask having the first opening 4*a* and the second opening 4*b* to prevent unintended light from leaking out of the first recess 20a and to prevent unintended external light from entering the second recess 20b.

The ground conductor layer 4 also functions as an electromagnetic shield to prevent external electromagnetic waves from entering the first recess 20a and the second recess 20b.

Electromagnetic waves entering the first recess 20a and the second recess 20b can be received by bonding wires that electrically connect the measurement sensor package 1, the light emitter, and the light receiver together. The bonding wires can thus serve as antennas to receive the electromagnetic waves and generate noise. The ground conductor layer 4 arranged on the main surface of the lid 3 excluding the first opening 4a and the second opening 4b allows passage of light, but prevents entrance of electromagnetic waves, thus reducing noise.

The ground conductor layer 4 arranged on the lid 3 reduces susceptibility to noise and improves the measurement accuracy.

The ground conductor layer 4 may be formed as a metal thin film by, for example, vapor deposition, sputtering, or baking of a metal material such as metals including Cr, Ti, Al, Cu, Co, Ag, Au, Pd, Pt, Ru, Sn, Ta, Fe, In, Ni, and W or an alloy of these metals, on the surface of the lid 3 formed from a transparent ceramic material or a glass material. The ground conductor layer 4 has a thickness of, for example, 500 to 4000 Å. The ground conductor layer 4 may be a single layer or a laminate of multiple layers.

In the measurement sensor including the measurement sensor package 1 according to the present embodiment, light emitted from the light emitter is partially reflected by the ground conductor layer 4 and becomes stray light toward the first step surface 20f. The first step surface 20f reflects such stray light back outside. Such reflection of stray light on the first step surface 20f can lower the measurement accuracy of the measurement sensor. In the present embodiment, the first step surface 20f has a smaller area than the second step surface 20g to prevent the measurement accuracy from decreasing. The first step surface 20f and the second step surface 20g may each be square or rectangular, or may have another shape. The first step surface 20f has, for example, a vertical dimension of 0.3 to 1.5 mm and a horizontal dimension of 0.1 to 1.0 mm. The second step surface 20g has, for example, a vertical dimension of 0.5 to 2.0 mm and a horizontal dimension of 0.2 to 1.5 mm.

A measurement sensor used for measuring blood flow or other purposes includes a light receiver that receives a relatively small amount of light and outputs a weak electric signal. Such a measurement sensor can perform accurate measurement by reducing electric resistance of a signal wiring conductor for the light receiver to reduce attenuation of electric signals output from the light receiver. The structure according to the present embodiment includes the second connection pad 23b having a larger area than the first connection pad 23a in a plan view to reduce the electric resistance of the signal wiring conductor 23 for the light receiver. The first connection pad 23a and the second connection pad 23b may each be square or rectangular or have another shape. The first connection pad 23a and the second connection pad 23b may cover the entire or partial areas of the first step surface 20f and the second step surface 20g. The first connection pad 23a has, for example, a vertical dimension of 0.1 to 1.5 mm, and a horizontal dimension of 0.1 to 1.0 mm. The second connection pad 23b has, for example, a vertical dimension of 0.2 to 2.0 mm, and a horizontal dimension of 0.1 to 1.5 mm.

A measurement sensor used for measuring blood flow or other purposes includes signal conductors that transmit relatively weak electric signals and are susceptible to internally occurring parasitic capacitance. For example, a difference between the parasitic capacitance generated in the light emitter and the parasitic capacitance generated in the light receiver lowers the measurement accuracy. In the present embodiment as described above, the second connection pad 23b has a larger area than the first connection pad 23a in a plan view. In the structure according to the present embodiment, a distance h1 between the first connection pad 23a and the ground conductor layer 4 in the thickness direction of the substrate 2 is smaller than a distance h2 between the second connection pad 23b and the ground conductor layer 4 in the thickness direction of the substrate 2. The structure according to the present embodiment reduces the difference between the parasitic capacitance caused between the ground conductor layer 4 and the first connection pad 23a and the parasitic capacitance between the ground conductor layer 4 and the second connection pad 23b, thus preventing the measurement accuracy from decreasing. For example, the distance h1 is 0.05 to 0.7 mm, and the distance h2 is 0.1 to 1.2 mm.

In the present embodiment, the substrate 2 also includes ground via conductors 21. The ground via conductors 21 are located outward from the first recess 20a and the second recess 20b in the substrate 2 in a plan view, and connected to the ground potential. The ground via conductors 21 include multiple feedthrough conductors connected together in the thickness direction of the substrate 2. The feedthrough conductors extend through the dielectric layers constituting the substrate 2 in the thickness direction. In the present embodiment, the ground via conductors 21 extend through the entire substrate 2 in the thickness direction as shown in, for example, FIG. 2. In a plan view, the feedthrough conductors in the dielectric layers are located at the same positions. More specifically, the ground via conductors 21 extend linearly through the substrate 2 from the first surface (first main surface) 20c to a second surface (second main surface) opposite to the first surface. Each ground via conductor 21 has a first end face 21a exposed on the first main surface 20c of the substrate 2, and a second end face 21b exposed on the second main surface of the substrate 2.

Each ground via conductor 21 has the first end face 21a connected to the ground conductor layer 4 arranged on the lid 3 with an annular ground conductor layer 22 (described later). The ground via conductors 21 have the second end faces 21b connected to external connection terminals 24 arranged on the second main surface of the substrate 2. The ground conductor layer 4 arranged on the lid 3 and the annular ground conductor layer 22 are electrically connected together by the ground via conductors 21 and have the same ground potential.

When a human finger, which is an example of a measurement object, touches the measurement sensor including the measurement sensor package 1 for measuring blood flow, electric charge from the human finger flows through the ground via conductors 21 from the first main surface 20c of the substrate 2 to the second surface (second main surface) of the substrate 2 is discharged outside.

However, in a known structure including no ground via conductors 21, electric charge from a human enters signal wiring conductors through, for example, a bonding wire, which is an example of a connector for electrically connecting the measurement sensor package 1 to the light emitter or the light receiver, and generates noise.

In the present embodiment, the ground via conductors 21 define a path that allows electric charge from a human to easily flow in the measurement sensor package 1 to guide the electric charge on the path and discharge the electric charge outside. The structure according to the present embodiment thus prevents the electric charge from entering the signal wiring conductors.

In the present embodiment, the ground via conductors 21 are arranged along the contour of the substrate 2. The substrate 2 has a rectangular contour, and the ground via conductors 21 are arranged along the rectangle. More specifically, the ground via conductors 21 are spaced equally from each side of the substrate 2 defining its contour line. In the plan view of FIG. 1, the ground via conductors 21 are drawn with dotted circles. For example, three ground via conductors 21 shown in the cross-sectional view of FIG. 2 are arranged at equal distances in the horizontal direction in an upper part of FIG. 1. The virtual straight line connecting the centers of the ground via conductors 21 extends parallel to the long sides of the substrate 2. The other ground via conductors 21 are also arranged similarly. For example, two ground via conductors 21 vertically arranged in a left portion of FIG. 1 are arranged to have the virtual straight line connecting the centers of the ground via conductors 21 parallel to the short sides of the substrate 2. Two ground via conductors 21 arranged horizontally in a lower part of FIG. 1 are arranged to have the virtual straight line connecting the centers of the ground via conductors 21 parallel to the long sides of the substrate 2.

In the present embodiment, the five ground via conductors 21 in total are arranged along the rectangular contour of the substrate 2 outward from and to surround the first recess 20a and the second recess 20b. The ground via conductors 21 are arranged at three of the four corners of the rectangle excluding one corner.

The ground via conductors 21 may be arranged based on the distances from the first recess 20a and the second recess 20b. As described above, the ground via conductors 21 transmit unintended electric charge that would generate noise when entering the signal wiring conductors. In this structure, each ground via conductor 21 and the signal wiring conductor 23 (including a conductor included in the substrate 2 and a bonding wire) formed in the measurement sensor package 1 are spaced from each other by at least a predetermined distance to prevent unintended electric charge from entering the signal wiring conductor 23 from the ground via conductors 21.

The ground via conductors 21 may not be arranged at any corner spaced by a distance shorter than a predetermined distance from the first recess 20a or the second recess 20b or in other words by a distance shorter than a predetermined distance from the signal wiring conductors 23, among the four corners of the rectangle in the present embodiment. In the present embodiment, the ground via conductor 21 is not arranged at one corner spaced by a distance shorter than a predetermined distance from the signal wiring conductor 23.

As described above, each ground via conductor 21 may have low electric resistance to guide unintended electric charge out of the package, and may have a larger diameter to have low electric resistance. However, any ground via conductor 21 having an excessively large diameter may be so close to the signal wiring conductor as to allow unintended electric charge to enter the signal wiring conductor through the ground via conductor 21. Considering these, each ground via conductor 21 may have a diameter D of, for example, 10 to 500 µm.

The annular ground conductor layer 22 is on the first main surface 20c of the substrate 2 to surround the openings of the first recess 20a and the second recess 20b. The annular conductor layer electrically connected to the first end faces 21a of the ground via conductors 21 exposed on the first main surface 20c of the substrate 2. To bond the lid 3 to the substrate 2, the annular ground conductor layer 22 is bonded to the ground conductor layer 4 using a molten-metal-based bond such as solder, Au—Sn, or a brazing material, or a resin-based bond such as an epoxy resin, a silicone resin, a thermoplastic resin, an anisotropic electroconductive resin, an electroconductive epoxy resin, or an electroconductive silicone resin.

The multiple ground via conductors 21 are arranged along the rectangular contour of the substrate 2, and the first end faces 21a are exposed on the first main surface 20c of the substrate 2 along the rectangular contour of the substrate 2. In the present embodiment, as shown in FIG. 1, the annular ground conductor layer 22 to be electrically connected to the first end faces 21a is rectangular in correspondence with the arrangement positions of the first end faces 21a. The annular ground conductor layer 22 includes lands 22a, which are connected to the first end faces 21a of the ground via conductors 21, and linear connectors 22b connecting the lands. Each land 22a is larger than the first end face 21a of the corresponding ground via conductor 21 for secure connection to the first end face 21a with low resistance. For example, each land 22a has a width or a diameter of 1×D to 3×D (one to three times the diameter), where D is the diameter of the first end face 21a of the corresponding ground via conductor 21. The linear connectors 22b are thinner than the lands 22a and have a uniform width.

Each signal wiring conductor 23 is electrically connected to the light emitter or the light receiver to transmit electric signals input to the light emitter or output from the light receiver. Each signal wiring conductor 23 according to the present embodiment includes a bonding wire, which is a connector connected to the light emitter or the light receiver, the first connection pad 23a and the second connection pad 23b to which the bonding wire is connected, signal via conductors 23c, which are electrically connected to the first connection pad 23a and the second connection pad 23b and extend linearly from immediately below the connection pads to the second main surface of the substrate 2, and an external connection terminal 24. The external connection terminal 24 is to be electrically connected to a connection terminal of an external mounting board, on which the measurement sensor including the measurement sensor package 1 is mountable, with a bond such as solder.

The annular ground conductor layer 22 and the external connection terminal 24 may be, for example, sequentially plated with a nickel layer having a thickness of 0.5 to 10 µm and a gold layer having a thickness of 0.5 to 5 µm to improve wettability with the bond such as solder and corrosion resistance.

The substrate 2, which can contain the light emitter and the light receiver and includes the ground via conductors 21 and the signal wiring conductors 23, may be a ceramic wiring board including dielectric layers formed from a ceramic insulating material, and the ground via conductors 21 and the signal wiring conductors 23 formed from a conductive material. The substrate 2 may also be an organic wiring board including dielectric layers formed from a resin insulating material.

The substrate 2 that is a ceramic wiring board includes dielectric layers formed from a ceramic material, through which conductors are arranged. The ceramic wiring board is formed from multiple ceramic dielectric layers.

Examples of the ceramic material used for the ceramic wiring board include sintered aluminum oxide, sintered mullite, sintered silicon carbide, sintered aluminum nitride, sintered silicon nitride, and sintered glass ceramic.

The substrate 2 that is an organic wiring board includes insulating layers formed from an organic material, through which conductors are arranged. The organic wiring board is formed from multiple organic dielectric layers.

The organic wiring board may be any wiring board having dielectric layers formed from an organic material, such as a printed wiring board, a build-up wiring board, or a flexible wiring board. Examples of the organic material used for an organic wiring board include an epoxy resin, a polyimide resin, a polyester resin, an acryl resin, a phenol resin, and a fluorine-based resin.

Figure 4:
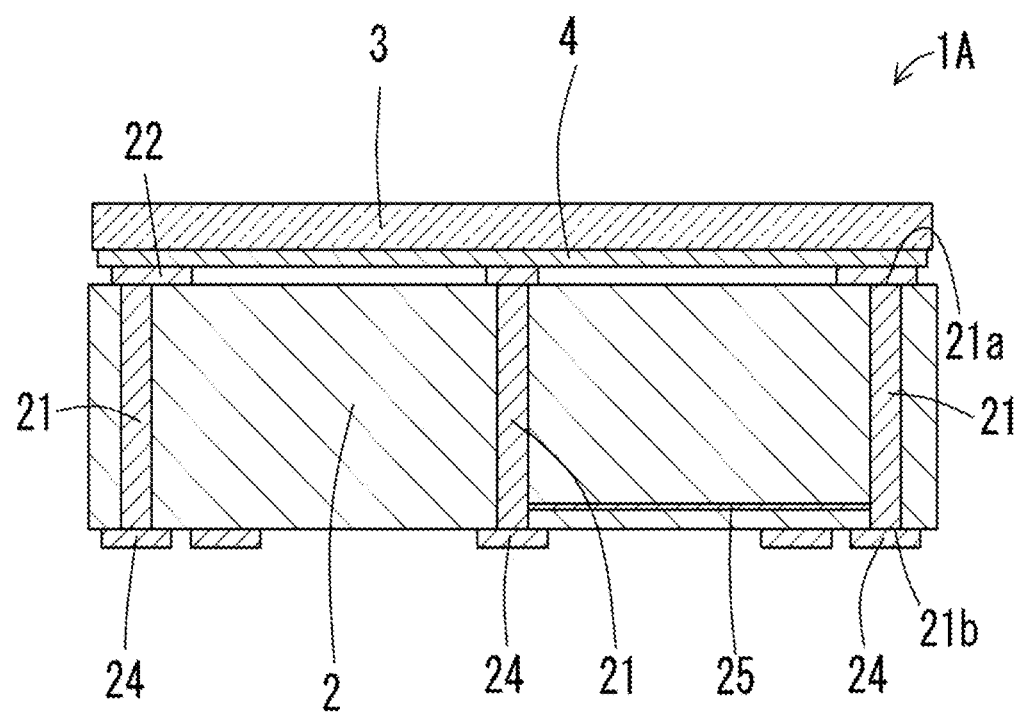
FIG. 4 is a cross-sectional view of a measurement sensor package 1A corresponding to the cross-sectional view of FIG. 2.
Figure 5:
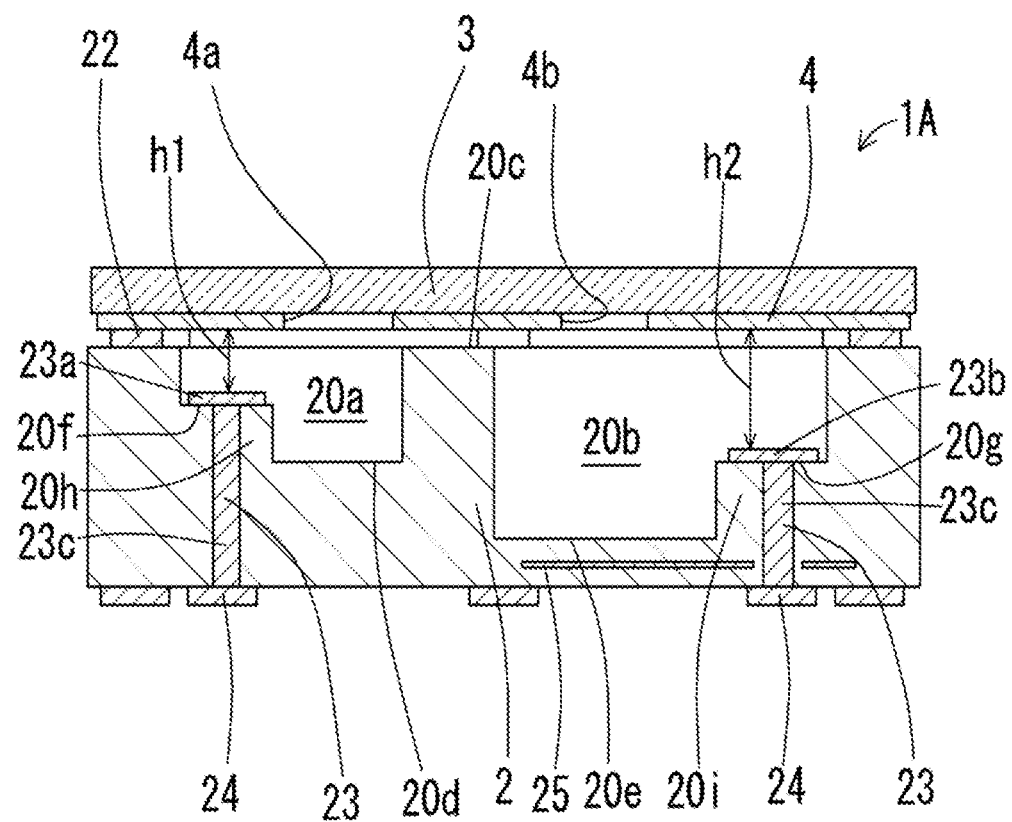
FIG. 5 is a cross-sectional view of the measurement sensor package 1A corresponding to the cross-sectional view of FIG. 3.

Other embodiments of the present invention will now be described. FIG. 4 is a cross-sectional view of a measurement sensor package 1A corresponding to the cross-sectional view of FIG. 2. FIG. 5 is a cross-sectional view of the measurement sensor package 1A corresponding to the cross-sectional view of FIG. 3.

The measurement sensor package 1A according to the present embodiment differs from the measurement sensor package 1 according to the above embodiment in that the substrate 2 further includes an internal ground conductor layer 25. The measurement sensor package 1A has the same other components. The same components are given the same reference signs as those of the measurement sensor package 1, and will not be described in detail.

The internal ground conductor layer 25 is connected to the ground potential, and arranged between the bottom of the second recess 20b and the second main surface of the substrate 2. The internal ground conductor layer 25 is electrically connected to the ground via conductors 21 in the substrate 2 and provided with the ground potential.

A measurement sensor used for measuring blood flow or other purposes includes a light receiver that receives a relatively small amount of light and outputs a weak electric signal. The electric signal is thus more susceptible to noise than an electric signal for controlling light emission input to the light emitter.

The measurement sensor is mounted on an external mounting board for use. An electromagnetic wave resulting from, for example, signals flowing through the wiring of the external mounting board may enter the measurement sensor package 1 from the second main surface of the substrate 2, and may generate noise in signals flowing through the signal wiring conductors 23.

As described above, the light receiver is particularly susceptible to noise. To reduce susceptibility to noise from the external mounting board, the internal ground conductor layer 25 is arranged between the bottom of the second recess 20b, which contains the light receiver, and the second main surface. The internal ground conductor layer 25 arranged between the second recess 20b and the external mounting board functions as an electromagnetic shield.

The measurement sensor package 1A according to the present embodiment includes the internal ground conductor layer 25 to reduce susceptibility to noise, and improves the measurement accuracy further.

A method for manufacturing the measurement sensor package 1 will now be described. First, the substrate 2 is formed with a method similar to a method for manufacturing a known multi-layer wiring board. For the substrate 2 that is a ceramic wiring board using alumina as a ceramic material, the powders of raw materials such as alumina ($Al_2O_3$), silica ($SiO_2$), calcium oxide (CaO), and magnesia (MgO) are mixed with an appropriate organic binder and an appropriate solvent to form slurry. The slurry is then shaped into a sheet using a known method such as a doctor blade or by calendering to obtain a ceramic green sheet (hereafter also referred to as a green sheet). The green sheet then undergoes punching into a predetermined shape. The powders of raw materials such as tungsten (W) and a glass material are mixed with an organic binder and a solvent to form a metal paste. The metal paste is then applied in a predetermined pattern by, for example, screen printing on the surface of the green sheet. The green sheet has through-holes formed and filled with the metal paste by, for example, screen printing to form via conductors. Multiple green sheets prepared in this manner are stacked on one another, and then fired together at about 1600° C. to complete the substrate 2.

The lid 3 is prepared by, for example, machining or cutting a glass material into a predetermined shape. The ground conductor layer 4, which is a metal thin film, is formed on the main surface of the lid 3 by, for example, vapor deposition, sputtering, or baking. The first opening 4a and the second opening 4b can be formed by patterning the metal thin film by, for example, photolithography (wet etching) or dry etching.

Figure 6:
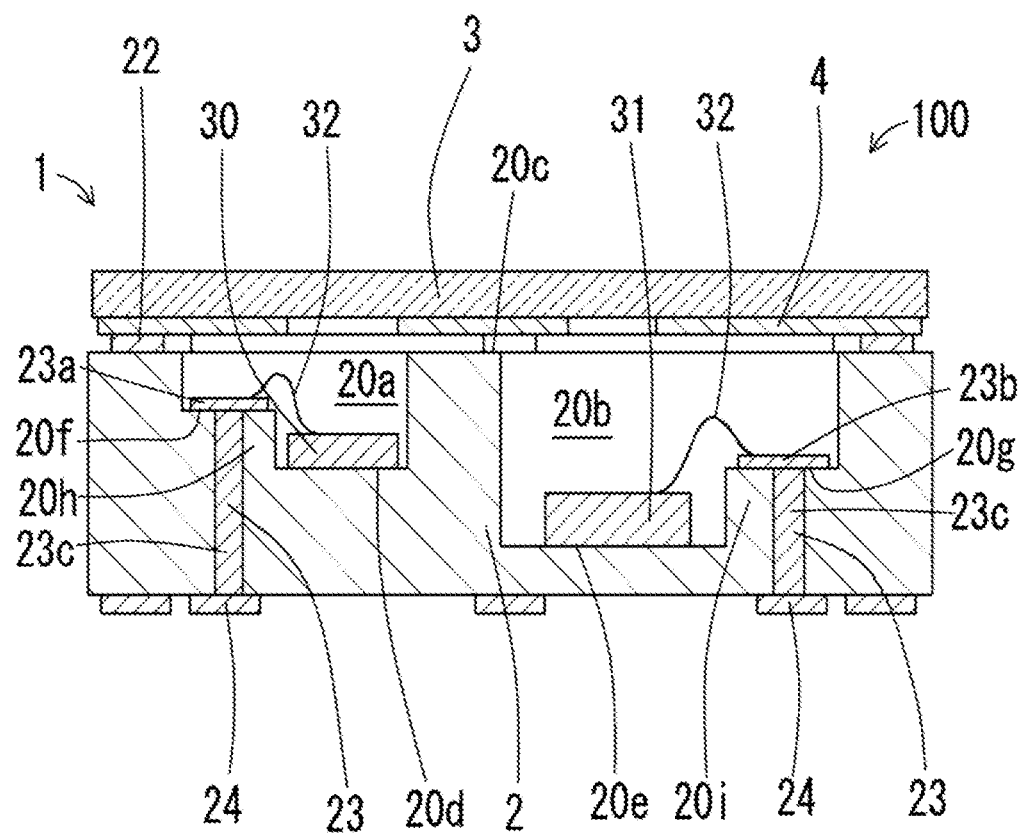
FIG. 6 is a cross-sectional view of the structure of a measurement sensor 100.

A measurement sensor 100 according to another embodiment of the present invention will now be described. FIG. 6 is a cross-sectional view of the measurement sensor 100 showing its structure. The measurement sensor 100 includes the measurement sensor package 1 or 1A, a light emitter 30, which is contained in a first recess 20a, and a light receiver 31, which is contained in a second recess 20b. The light emitter 30 is mounted on a first bottom surface 20d of the first recess 20a. The light receiver 31 is mounted on a second bottom surface 20e of the second recess 20b. The measurement sensor 100 is obtained by connecting the light emitter 30 to a first connection pad 23a and connecting the light receiver 31 to a second connection pad 23b both using bonding wires 32, and joining the lid 3 to the substrate 2.

The light emitter 30 may be formed from a semiconductor laser element such as a vertical cavity surface emitting laser (VCSEL). The light receiver 31 may be formed from a photodiode such as a silicon photodiode, a GaAs photodiode, an InGaAs photodiode, or a germanium photodiode. The light emitter 30 and the light receiver 31 may be appropriately selected in accordance with the type of a measurement object or the parameters to be measured.

For example, a VCSEL that can emit a laser beam with a wavelength of 850 nm may be used as the light emitter 30 for measuring blood flow using the optical Doppler effect. To measure another object, another device that emits a laser beam with a wavelength appropriate for the measurement object may be selected as the light emitter 30. With a laser beam emitted from the light emitter 30 and having its wavelength unchanged, any light receiver that can receive such a beam may be used as the light receiver 31. With a laser beam emitted from the light emitter 30 and having its wavelength changed, any light receiver that can receive such a beam with its wavelength changed may be used as the light receiver 31.

Although the light emitter 30 is electrically connected to the first connection pad 23a and the light receiver 31 is electrically connected to the second connection pad 23b with, for example, the bonding wires 32 in the present embodiment, the connection may be achieved with another method, such as flip chip connection, a method using bumps, or a method using an anisotropic conductive film.

The measurement sensor 100 is mounted on an external mounting board for use. For example, a control unit for controlling light emission of the light emitter 30, and an arithmetic unit that calculates the blood flow rate and other parameters based on signals output from the light receiver 31 are also mounted on the external mounting board.

To start measurement, the fingertip of a finger, which is a measurement object, is placed into contact with the surface of the lid 3, and a light emitter control current is input from the external mounting board into the measurement sensor 100 through the external connection terminal 24, and input to the light emitter 30 through a signal via conductor 23c and the second connection pad 23b. Light for measurement is then emitted from the light emitter 30. When the emitted light passes through a first opening 4a and is applied to the fingertip through the lid 3, the light is scattered by blood cells in the blood. When receiving the scattered light transmitted through the lid 3 and passing through a second opening 4b, the light receiver 31 outputs an electric signal corresponding to the amount of received light. The output signal then passes through the first connection pad 23a and the signal via conductor 23c, and is output from the measurement sensor 100 to the external mounting board through the external connection terminal 24.

In the external mounting board, a signal output from the measurement sensor 100 is input to the arithmetic element, which can then calculate the blood flow rate based on, for example, the frequency of the illuminating light emitted from the light emitter 30 and the frequency of the scattered light received by the light receiver 31.

In the above structure, the ground via conductors 21 vertically extend linearly in the substrate 2. The ground via conductors 21 may not extend linearly, and may be displaced inside the substrate 2 due to, for example, an inner layer wire or the internal ground conductor layer 25 when the substrate 2 has the first main surface 20c electrically connected to the external connection terminals 24 on the second main surface.

In the present embodiment, the annular ground conductor layer 22 may be optional. The ground conductor layer 4 on the lid 3 and the ground via conductors 21 may be directly joined together for electrical connection between them.

The internal ground conductor layer 25 may further extend in the plane direction from a portion between the bottom of the second recess 20b and the second main surface of the substrate 2 and may be located between the bottom of the first recess 20a and the second main surface.

EXAMPLES

The amount of cross-talk between the first and second connection pads 23a and 23b was calculated through simulation for a measurement sensor package according to example 1. The measurement sensor package according to example 1 is similar to the measurement sensor package 1 shown in FIGS. 1 to 3 except that the first recess 20a and the second recess 20b have the same depth in the thickness direction of the substrate 2, and the distance between the first step surface 20f and the first main surface 20c of the substrate 2 is equal to the distance between the second step surface 20g and the first main surface 20c of the substrate 2. The first connection pad 23a has a vertical dimension of 1.0 mm and a horizontal dimension of 0.5 mm. The second connection pad 23b has a vertical dimension of 1.0 mm and a horizontal dimension of 0.5 mm. In a plan view, the distance between the centers of the first connection pad 23a and the second connection pad 23b is 3.0 mm. The depth of the first recess 20a and the depth of the second recess 20b are 1.0 mm. In the thickness direction of the substrate 2, the distance between the first step surface 20f and the first main surface 20c of the substrate 2 and the distance between the second step surface 20g and the first main surface 20c of the substrate 2 are 0.25 mm.

The measurement sensor package 1 used in the simulation eliminates components other than the substrate 2, the first connection pad 23a, and the second connection pad 23b, and the substrate 2 as a perfect conductor. Under such conditions, the frequency dependence of the amount of cross-talk between the first and second connection pads 23a and 23b was calculated with a method described below. A voltage signal output from the second connection pad 23b in response to an input of the voltage signal to the first connection pad 23a was calculated. The logarithm of the ratio of the strength of the output voltage signal to the strength of the input voltage signal was multiplied by a predetermined coefficient to obtain the amount of cross-talk. The frequency dependence of the amount of cross-talk was calculated with the frequency of the input voltage being varied in the range of 1 to 20 kHz. In this simulation, a larger absolute value of the amount of cross-talk indicates that the first connection pad 23a and the second connection pad 23b can be shielded electrically more efficiently, and electric cross-talk between the first and second connection pads 23a and 23b is reduced more effectively.

The frequency dependence of the amount of cross-talk between the first and second connection pads 23a and 23b was calculated for a measurement sensor package according to comparative example 1 under the same conditions as in the simulation for the measurement sensor package according to example 1. The measurement sensor package according to comparative example 1 is similar to the measurement sensor package 1 according to example 1 except that the first step surface 20f is located inward from the first bottom surface 20d and the second step surface 20g is located inward from the second bottom surface 20e in a plan view in the direction connecting the centers c1 and c2 of the first and second bottom surfaces 20d and 20e. In comparative example 1, the distance between the center of the first connection pad 23a and the center of the second connection pad 23b is 1.0 mm in a plan view.

The frequency dependence of the amount of cross-talk between the first and second connection pads 23a and 23b was calculated for the measurement sensor package 1 shown in FIGS. 1 to 3 in example 2 under the same conditions as in the simulation for example 1. In example 2, the first recess 20a has a depth of 1.0 mm, and the second recess 20b has a depth of 2.0 mm. In the thickness direction of the substrate 2, the distance between the first step surface 20f and the first main surface 20c of the substrate 2 is 0.25 mm, and the distance between the second step surface 20g and the first main surface 20c of the substrate 2 is 0.75 mm.

The frequency dependence of the amount of cross-talk between the first and second connection pads 23a and 23b was calculated for a measurement sensor package according to comparative example 2 under the same conditions as in the simulation for the measurement sensor package according to example 1. The measurement sensor package according to comparative example 2 is similar to the measurement sensor package 1 according to example 2 except that the first step surface 20f is located inward from the first bottom surface 20d and the second step surface 20g is located inward from the second bottom surface 20e in a plan view in the direction connecting the centers c1 and c2 of the first and second bottom surfaces 20d and 20e. In comparative example 2, the distance between the center of the first connection pad 23a and the center of the second connection pad 23b is 1.0 mm in a plan view.

Figure 7A:
FIGS. 7A to 7D are graphs showing the simulation results for the amount of cross-talk in examples and comparative examples.
Figure 7B:
Figure 7C:
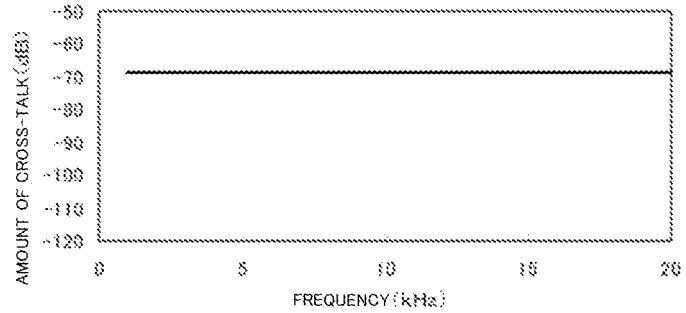
Figure 7D:
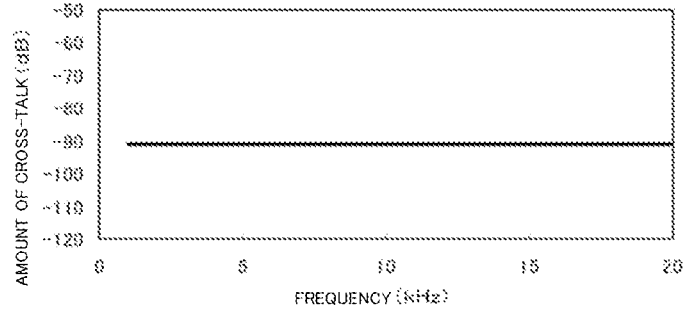

FIGS. 7A to 7D are graphs showing the results in the above examples and comparative examples. FIG. 7A shows the results in comparative example 1. FIG. 7B shows the results in example 1. FIG. 7C shows the results in comparative example 2. FIG. 7D shows the results in example 2. As shown in FIGS. 7A to 7D, the results in example 1, example 2, comparative example 1, and comparative example 2 all show that the amount of cross-talk does not depend on the frequency of the input voltage. This is seemingly because the amount of cross-talk in the simulation substantially depends solely on the length of the electric path in the substrate 2 between the first and second connection pads 23a and 23b, and the electric paths have substantially the same length for voltage signals with the frequency bandwidth of 1 to 20 kHz. As shown in FIGS. 7A and 7B, the amount of cross-talk is smaller in example 1 than in comparative example 1 within the full frequency bandwidth of 1 to 20 kHz. As shown in FIGS. 7C and 7D, the amount of cross-talk in example 2 is smaller than the amount of cross-talk in comparative example 2 within the full frequency bandwidth of 1 to 20 kHz.

Figure 8:
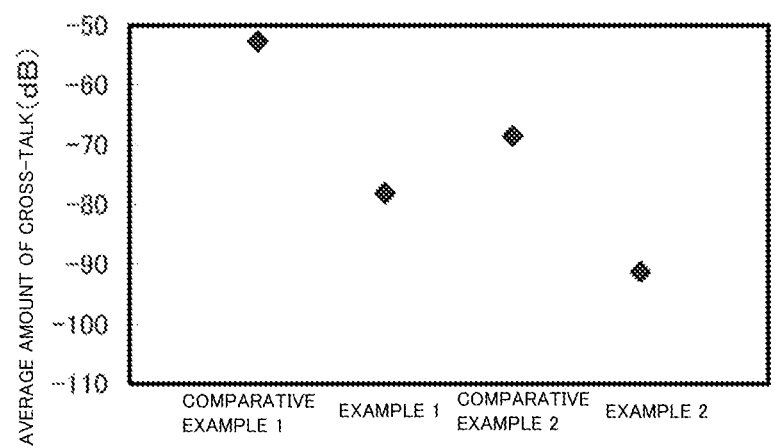
FIG. 8 is a graph showing the evaluation results in the examples and the comparative examples.

FIG. 8 is a graph showing the evaluation results in example 1, example 2, comparative example 1, and comparative example 2. The average amount of cross-talk is used as the evaluation result. The average amount of cross-talk is the amount across the frequency bandwidth of 1 to 20 kHz. A larger average amount of cross-talk indicates a smaller amount of electric cross-talk. A smaller average amount of cross-talk indicates reduced electric cross-talk.

As shown in FIG. 8, the average amount of cross-talk is smaller in example 1 than in comparative example 1, indicating reduced electric cross-talk. The average amount of cross-talk is smaller in example 2 than in comparative example 2, indicating reduced electric cross-talk. The average amount of cross-talk is smaller in example 1 than in comparative example 2. More specifically, the first step surface 20f located outward from the first bottom surface 20d and the second step surface 20g located outward from the second bottom surface 20e in the direction connecting the centers c1 and c2 of the first and second bottom surfaces 20d and 20e in a plan view can more effectively reduce electric cross-talk between the first connection pad 23a and the second connection pad 23b than the first recess 20a less deep than the second recess 20b.

As described above, the results in example 1 and example 2 reveal that the first step surface 20f located outward from the first bottom surface 20d and the second step surface 20g located outward from the second bottom surface 20e in the direction connecting the centers c1 and c2 of the first and second bottom surfaces 20d and 20e in a plan view more effectively reduce electric cross-talk between the light emitter and the light receiver.

The present invention may be embodied in various forms without departing from the spirit or the main features of the present invention. The embodiments described above are thus merely illustrative in all respects. The scope of the present invention is defined not by the description given above but by the claims, and any modifications and alterations contained in the claims fall within the scope of the present invention.

REFERENCE SIGNS LIST 1 measurement sensor package
1A measurement sensor package
2 substrate
3 lid
4 ground conductor layer
4a first opening
4b second opening
20a first recess
20b second recess
20c first surface
20d first bottom surface
20e second bottom surface
20f first step surface
20g second step surface
20h first step
20i second step
21 ground via conductor
21a first end face
21b second end face
22 annular ground conductor layer
22a land
22b linear connector
23 signal wiring conductor
23a first connection pad
23b second connection pad
23c signal via conductor
24 external connection terminal
25 internal ground conductor layer
30 light emitter
31 light receiver
32 bonding wire
100 measurement sensor

The invention claimed is:

1. A measurement sensor package, comprising:
a substrate including a plurality of dielectric layers stacked on one another, the substrate being a rectangular plate and including a first recess and a second recess formed within a first surface thereof, the first recess being configured to contain a light emitter, the second recess being configured to contain a light receiver, the second recess being different and separate from the first recess,
the first recess including a first bottom surface on which the light emitter is mountable, and an inner side surface having a first step with a first step surface extending in a plane direction of the first surface,
the first step surface having a first connection pad thereon, the first connection pad being electrically connectable to the light emitter,
the second recess including a second bottom surface on which the light receiver is mountable, and an inner side surface having a second step with a second step surface extending in the plane direction of the first surface,
the second step surface having a second connection pad thereon, the second connection pad being electrically connectable to the light receiver,
wherein in a direction connecting a center of the first bottom surface and a center of the second bottom surface in a plan view, the first step surface is located outward from the first bottom surface and the second step surface is located outward from the second bottom surface,
the first step surface is located between the first bottom surface and the first surface in a vertical direction, and the second step surface is located between the second bottom surface and an internal portion of the first surface in the vertical direction, a first signal via conductor connecting from the first connection pad on the first step surface to an external connection terminal through the substrate, and a second signal via conductor connecting from the second connection pad on the second step surface to the external connection terminal through the substrate.

2. The measurement sensor package according to claim 1, further comprising:

a lid being a plate covering the first recess and the second recess, the lid comprising an insulating material, the lid being configured to transmit light emitted from the light emitter contained in the first recess and to transmit light to be received by the light receiver contained in the second recess; and a ground conductor layer located on a main surface of the lid facing the first recess and the second recess and connected to a ground potential, the ground conductor layer having a first opening configured to allow passage of light emitted from the light emitter, and a second opening configured to allow passage of light to be received by the light receiver.

3. The measurement sensor package according to claim 2, wherein a distance between the first connection pad and the ground conductor layer is smaller than a distance between the second connection pad and the ground conductor layer in the thickness direction of the substrate.

4. The measurement sensor package according to claim 1, wherein the first step surface has a smaller area than the second step surface.

5. The measurement sensor package according to claim 1, wherein the second connection pad has a larger area than the first connection pad in the plan view.

6. A measurement sensor, comprising:

the measurement sensor package according to claim 1;

a light emitter contained in the first recess; and a light receiver contained in the second recess.

7. The measurement sensor package according to claim 2, wherein a distance between the first connection pad and the ground conductor layer is smaller than a distance between the second connection pad and the ground conductor layer in the thickness direction of the substrate.

8. The measurement sensor package according to claim 2, wherein the first step surface has a smaller area than the second step surface.

9. The measurement sensor package according to claim 2, wherein the second connection pad has a larger area than the first connection pad in the plan view.

10. The measurement sensor package according to claim 3, wherein the first step surface has a smaller area than the second step surface.

11. The measurement sensor package according to claim 3, wherein the second connection pad has a larger area than the first connection pad in the plan view.

12. The measurement sensor package according to claim 4, wherein the second connection pad has a larger area than the first connection pad in the plan view.

13. The measurement sensor package according to claim 1, further comprising a plurality of ground via conductors provided outside the first recess and the second recess.

14. The measurement sensor package according to claim 1, further comprising an internal grounding conductor layer positioned at a position overlapping the second bottom surface of the second recess.

* * * * *